United States Patent [19]

Rauchschwalbe et al.

[11] Patent Number: 5,672,708

[45] Date of Patent: Sep. 30, 1997

[54] PROCESS FOR THE PREPARATION OF N-ARYLAMINOACRYLIC ACID DERIVATIVES AND THE USE OF N-ARYLAMINOACRYLIC ACID DERIVATIVES THUS PREPARED FOR THE PREPARATION OF 4-QUINOLONE-3-CARBOXYLIC ACID DERIVATIVES

[75] Inventors: Günter Rauchschwalbe, Leverkusen; Bernhard Beitzke, Rösrath; Wolfgang Eymann, Köln; Helmut Fiege, Leverkusen, all of Germany

[73] Assignee: Bayer Aktiengesellschaft, Leverkusen, Germany

[21] Appl. No.: 521,941

[22] Filed: Aug. 31, 1995

[30] Foreign Application Priority Data

Sep. 7, 1994 [DE] Germany .......................... 44 31 821.9

[51] Int. Cl.[6] ...................... C07D 491/02; C07D 307/00; C07C 205/00; C07C 229/00

[52] U.S. Cl. ..................... 546/115; 546/255; 546/256; 546/262; 546/264; 549/430; 549/357; 549/512; 560/21; 560/43; 562/435; 562/456

[58] Field of Search ........................ 546/115, 255, 546/256, 262, 264; 560/21, 43; 562/435, 456; 549/430, 357, 512

[56] References Cited

U.S. PATENT DOCUMENTS

| | | | |
|---|---|---|---|
| 4,994,599 | 2/1991 | Chu .................................. | 560/43 |
| 5,030,747 | 7/1991 | Blank et al. ..................... | 560/172 |
| 5,182,401 | 1/1993 | Grohe .............................. | 546/287 |
| 5,241,099 | 8/1993 | Blank et al. ..................... | 558/375 |
| 5,401,869 | 3/1995 | Kraus et al. ..................... | 558/375 |

FOREIGN PATENT DOCUMENTS

| | | |
|---|---|---|
| 0388744 | 9/1990 | European Pat. Off. . |
| 0457090 | 11/1991 | European Pat. Off. . |
| 0504693 | 9/1992 | European Pat. Off. . |
| 0565132 | 10/1993 | European Pat. Off. . |
| 0608725 | 8/1994 | European Pat. Off. . |
| 9085255 | 3/1990 | Japan . |

OTHER PUBLICATIONS

Chemical Abstracts, vol. 113, abstract No. 113: 132028b, p. 636, abstract of JP 02-85,255, (1990).

R.G. Jones, J. Am. Chem. Soc., vol. 74, pp. 4889-4891, (1952).

D.T.W. Chu, et al., J. Med. Chem., vol. 28, No. 11, pp. 1558-1564, (1985).

M.P. Wentland, et al., J. Med. Chem., vol. 36, No. 11, pp. 1580-1596, (1993).

S. Rádl, et al., Collect. Czech. Chem. Commun., vol. 54, pp. 2181-2189, (1989).

*Primary Examiner*—Joseph Conrad
*Attorney, Agent, or Firm*—Sprung Horn Kramer & Woods

[57] ABSTRACT

N-arylaminoacrylic acid derivatives are obtained in good yields and in high purities when benzoylacetic acid derivatives are reacted with N-arylimino ethers. The products thus prepared are used, in particular, for the preparation of 4-quinolone-3-carboxylic acid derivatives, which have an outstanding bactericidal action.

5 Claims, No Drawings

PROCESS FOR THE PREPARATION OF N-ARYLAMINOACRYLIC ACID DERIVATIVES AND THE USE OF N-ARYLAMINOACRYLIC ACID DERIVATIVES THUS PREPARED FOR THE PREPARATION OF 4-QUINOLONE-3-CARBOXYLIC ACID DERIVATIVES

The present invention firstly relates to an advantageous process for the preparation of N-arylaminoacrylic acid derivatives which are otherwise accessible only in an unsatisfactory manner.

It is known to prepare N-arylaminoacrylic acid derivatives by subjecting benzoylacetic esters to a condensation reaction with a trialkyl orthoformate to give β-alkoxyacrylic ester derivatives and then reacting these with N-arylamines (cf. J. Med. Chem. 28, 1558–1564 (1985)). The condensation reaction with the trialkyl orthoformate must in this case be carried out in excess acetic anhydride. This acetic anhydride must be removed completely before the addition of the N-arylamine, because otherwise the N-arylamine reacts with the acetic anhydride. The absence of acetic anhydride during the condensation reaction with the trialkyl orthoformate leads to a drastic reduction in yield (cf. J. Am. Chem. Soc. 74, 4889 (1952)). The reaction temperature is 130° C. or higher. Highly colouring secondary components of unknown structure which can be removed only with difficulty are formed in this reaction.

Furthermore, in the second process step, the N-arylamine added can react not only in the desired position but also at other activated positions, for example on the aryl nucleus (in the p-position relative to the carbonyl group) or on the ester function (to form amide). Although these secondary reactions take place only to a minor extent, they are nevertheless extremely undesirable because they lead to a loss in yield and require additional separation effort. N-arylaminoacrylic acid derivatives are in fact intermediates for the preparation of pharmaceuticals and must therefore be prepared in the greatest possible purity.

The preparation of N-arylaminoacrylic acid derivatives via imino ethers is known only via a roundabout route (cf. EP-A1 565 132 and J. Med. Chem. 36, 1580 (1993)). In this preparation (substituted) benzoylacetic esters are reacted with N,N-dialkylformamide acetal to give dialkylenamines, which then in a second reaction stage with an N-arylamine lead to the desired product. An N,N-dialkylamine is liberated in this reaction and, for ecological reasons, must be separated and disposed of with great effort. Furthermore, N,N-dialkylamines tend to react with halogen atoms on aromatic rings under the formation conditions. Undesirable by-products are formed in these reactions and must be separated with considerable effort for the abovementioned reasons.

Certain N-arylaminoacrylic acid derivatives can also be obtained from N-unsubstituted quinolonecarboxylic acids by reaction with 4-nitrofluorobenzene (arylation), reduction and fluorination by the Balz-Schiemann method (cf. Collect. Czech. Chem. Commun. 54, 2181 (1989)). The overall yield of this multi-stage process is low (for example 61% in the arylation), and certain substitution patterns are not accessible in this manner.

A process has now been found for the preparation of N-arylaminoacrylic acid derivatives of the formula (I)

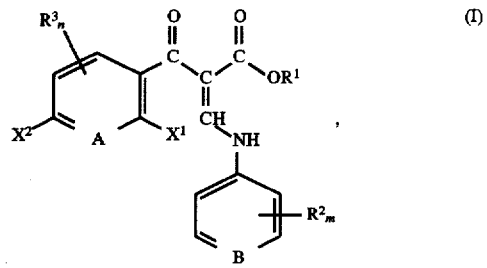

in which $R^1$ denotes hydrogen or $C_1$–$C_6$-alkyl, $R^2$ and $R^3$ independently of one another each denote fluorine, chlorine, bromine, trifluoromethyl, cyano, nitro, $C_1$–$C_6$-alkoxy, hydroxyl, imidazolyl, triazolyl or $C_7$–$C_{10}$-aralkoxy or $R^2$ and $R^3$ together denote an —O—, —$CH_2$—, —$CH_2O$—, —O—CH—O— or —O—$CH_2$—$CH_2$—O— radical, $X^1$ and $X^2$ independently of one another each denote fluorine, chlorine or bromine, A denotes CH, N or $CR^3$, where $R^3$=fluorine, chlorine, bromine, trifluoromethyl, cyano, nitro, $C_1$–$C_6$-alkoxy, hydroxyl, imidazolyl, triazolyl or $C_7$–$C_{10}$-aralkoxy, B denotes CH, N or $CR^2$, where $R^2$=fluorine, chlorine, bromine, trifluoromethyl, cyano, nitro, $C_1$–$C_6$-alkoxy, hydroxyl, imidazolyl, triazolyl or $C_7$–$C_{10}$-aralkoxy, m denotes zero, 1, 2 or 3 and n denotes zero, 1 or 2, which is characterized in that a benzoylacetic acid derivative of the formula

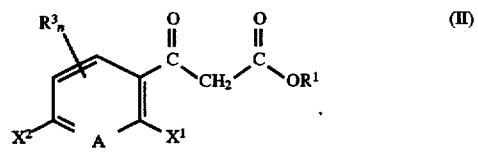

in which $R^1$, $R^3$, $X^1$, $X^2$, A and n have the meaning given for formula (I), is reacted with an N-arylimino ether of the formula

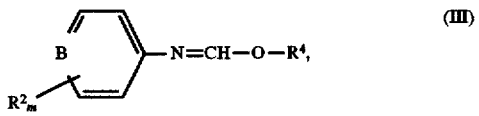

in which $R^2$, B and m have the meaning given for formula (I) and $R^4$ represents $C_1$–$C_6$-alkyl.

In the formulae (I) and (II), $R^1$ preferably represents $C_1$–$C_4$-alkyl, $R^3$ preferably represents fluorine or chlorine, $X^1$ and $X^2$ independently of one another preferably each represent fluorine or chlorine, A preferably represents CH or $CR^3$, where $R^3$=fluorine or chlorine, B preferably represents CH, N or $CR^2$, where $R^2$=F, Cl, Br or nitro, and n represents zero or 1.

In the formulae (I) and (III), $R^2$ preferably represents fluorine and m represents zero or 1.

In formula (II), $R^4$ preferably represents $C_1$–$C_4$-alkyl.

The starting substances for the process according to the invention are known. Benzoylacetic acid derivatives of the formula (II) and their preparation are described, for example, in Synthesis 1993, 290 and in U.S. Pat. No. 5,262,559. Benzoylacetic acid derivatives of the formula (II) which are particularly preferably to be employed are methyl 2,3,4,5-tetrafluorobenzoylacetate, methyl 2,4,5-trifluorobenzoylacetate, methyl 3-chloro-2,4,5-trifluorobenzoylacetate, methyl 2,4-dichloro-5-fluorobenzoylacetate, methyl 4-nitro-2-chlorobenzoylacetate, methyl 2,6-dichloro-5-fluoro-3-nicotinoylacetate, methyl 5,6-dibromo-3,4-dioxolobenzoylacetate and ethyl 4-bromo-2-chlorobenzoylacetate and the corresponding ethyl and methyl esters.

N-arylimino ethers of the formula (III) are described, for example, in DE-A 17 68 004, C.A. 64, 2024 and C.A. 84, 179 844. N-arylimino ethers of the formula (III) in which $R^4$ represents methyl or ethyl, the group $R_m^2$ represents 2-fluoro, 2-chloro, 3-trifluoromethyl, 2-trifluoromethyl or 3,4-methylenedioxy and B represents CH, N or $CR^2$, where $R^2$=F, Cl, Br or nitro, are particularly preferably employed.

The process according to the invention can be carried out, for example, at temperatures in the range from 30° to 130° C. Temperatures from 50° to 120° C., in particular those from 70° to 100° C., are preferred.

The process according to the invention can be carried out without a solvent. In this case, the temperature is expediently chosen at least high enough for the reaction mixture to form a melt. The reaction can also be carried out in the presence of inert solvents, for example in the presence of toluene, chlorobenzene, dichlorobenzene, oligoethylene glycol monoalkyl ethers, oligoethylene glycol dialkyl ethers, dimethylformamide or N-methylpyrrolidone. Preferred solvents are diethylene glycol monoalkyl ethers and diethylene glycol dialkyl ethers. Butoxyethanol and diglyme are particularly preferred.

Benzoylacetic acid derivatives of the formula (II) and N-arylimino ethers of the formula (III) can be employed, for example, in molar ratios of from 0.6 to 1.2:1. This ratio is preferably from 0.8 to 1.05:1.

To accelerate the reaction and in order to obtain a complete conversion, it is advantageous for the alcohol formed to be removed from the reaction mixture during the reaction, for example by distillation, if appropriate under reduced pressure.

If desired, the process according to the invention can be catalysed by addition of a small amount of a strong acid. Trifluoromethanesulphonic acid, for example, is suitable.

The reaction time for the process according to the invention can be, for example, between 1 and 10 hours. The reaction time is preferably in the range from 2 to 6 hours.

After the process according to the invention has been carried out, the N-arylaminoacrylic acid derivative of the formula (I) prepared is present in a high purity, usually more than 97%. In particular, it contains no colouring by-products, but often only small amounts of the starting substances employed and possibly residues of the alcohol split off. In most cases, the N-arylaminoacrylic acid derivative of the formula (I) prepared according to the invention can be used further directly without further purification. This also applies if the reaction has been carried out in the presence of a solvent. The solvent-containing product can then be used further directly.

If further purification is desired it can be carried out, for example, by recrystallization, for example from mixtures of lower alcohols and water. If the reaction has been carried out in a solvent, for example in diglyme, this can be removed, for example, by distillation under reduced pressure or by addition of water and removal of the product by filtration.

N-arylaminoacrylic acid derivatives of the formula (I) prepared according to the invention are particularly suitable for the preparation of corresponding 4-quinolone-3-carboxylic acid derivatives. The present invention therefore also relates to the use of N-arylaminoacrylic acid derivatives of the formula (I) prepared according to the invention for the preparation of 4-quinolone-3-carboxylic acid derivatives of the formula

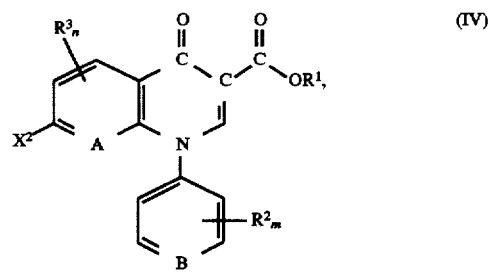

in which $R^1$, $R^2$, $R^3$, $X^2$, A, B, m and n have the meaning given for formula (I), by addition of an auxiliary base in the presence of a solvent.

Possible auxiliary bases are, for example, magnesium oxide and/or calcium oxide and possible solvents are, for example, those which can be employed, if appropriate, in the process according to the invention.

The preparation of the quinolonecarboxylic acid derivatives of the formula (IV) from the N-arylaminoacrylic acid derivatives of the formula (I) can be carried out, for example, at temperatures between 90° and 130° C., preferably between 100° and 120° C. Protic or aprotic solvents, for example, can be employed as solvents for this reaction, and toluene, chlorobenzene, dichlorobenzene, oligoethylene glycol mono- or dialkyl ethers, dimethylformamide and N-methylpyrrolidone are preferred. Polar solvents such as diethylene glycol mono- or dialkyl ethers are preferred, and butoxyethanol, diethylene glycol dimethyl ether and diethylene glycol diethyl ether are especially preferred. The solvents can be employed, for example, in an amount of from 400 to 1000 ml per mole of the compound of the formula (I). This amount is preferably from 500 to 600 ml per mole.

The auxiliary bases can be employed, for example, in amounts of from 0.5 to 3 mol per mole of the compound (I), and this amount is preferably from 1 to 2 mol.

The batches for the preparation according to the invention of quinolonecarboxylic acid derivatives of the formula (IV) can be worked up, for example, by adding water and acid, hydrolysing residual ester functions to the carboxylic acid by heating, dissolving inorganic constituents and separating off the desired product from the liquid phase by filtration. Possible acids are, for example, acetic acid, citric acid, sulphuric acid or hydrochloric acid, and the inorganic constituents can be, for example, residual auxiliary base.

It is particularly preferable for this utility not to isolate N-arylaminoacrylic acid derivatives of the formula (I) but to carry out the conversion to 4-quinolone-3-carboxylic acid derivatives of the formula (IV) in the same reaction vessel as for their preparation (=one-pot process). 4-Quinolone-3-carboxylic acid derivatives of the formula (IV) can be reacted with suitable amines to give highly active antibiotics (cf. U.S. Pat. No. 4,994,599).

It is decidedly surprising that benzoylacetic acid derivatives of the formula (II) and N-arylimino ethers of the formula (III) can be subjected to a condensation reaction under mild conditions to give N-arylaminoacrylic acid derivatives of the formula (I) in the manner according to the invention, and additionally in very high yields and purities.

Thus, for example, methyl 2,4-dichloro-5-fluorobenzoylacetate reacts practically completely with O-ethyl N-(4-fluorophenyl)-formiminoether without a solvent within a few hours even at 50° C., and in a moderately polar solvent within 3 hours at 50° C. The purity of the N-arylaminoacrylic acid derivatives of the formula (I) prepared is so high that the products can be processed further without intermediate isolation and purification, for example to give 4-quinolone-3-carboxylic acid derivatives of the formula (IV) which immediately meet pharmaceutical quality requirements. Yields of about 85% of theory, based on the N-arylimino ethers of the formula (II) employed, are in general achieved in the preparation of such 4-quinolone-3-carboxylic acid derivatives.

This is all the more astonishing since it was to be expected that N-arylimino ethers would be less reactive than N-alkylimino ethers, so that more drastic conditions than in known syntheses with N-alkylimino ethers would be necessary, which should lead to the formation of larger amounts of by-products and thus to poorer yields and purities. Similar syntheses with N-alkylimino ethers are described, for example, in Acta Chimica Academiae Scientiarum Hungarica 74 (3), 351–356 (1972), where temperatures of at least 140° C., reaction times of at least 24 hours, yields of not more than 68% and the impossibility of the preparation of N-aryl derivatives are mentioned (for the latter, cf. loc. cit. 78 (2), 217 and 223), and in J. Heterocyclic Chem. 24, 1537 (1987) and in loc. cit. 17, 1729 (1980). In the last two publications mentioned, at least 48 hours at 65° C. or, respectively, 72 hours at 110° to 115° C. are mentioned as the reaction conditions and yields of 80 and 56% of theory respectively are indicated.

EXAMPLES

Example 1

88 g (0.53 mol) of N-(4-fluorophenyl)-forminino ethyl ether were initially introduced into the reaction vessel and 132 g of methyl 2,4-dichloro-5-fluorobenzoylacetate (0.50 mol) were added. The mixture was heated to 100° C. in the course of 90 minutes, during which 22 g of ethanol and a little of the imino ether employed were distilled off under 200 mbar. 196 g of methyl 3-[N-(4-fluorophenylamino)]-2-(2,4-dichloro-5-fluorobenzoyl)-acrylate were obtained as a pale yellow product. According to the gas chromatogram, it contained 1% each of ethanol and the imino ether employed.

Example 2

The reactants were brought together in the same amounts as in Example 1 and then left to stand in an open glass beaker for 2½ days at 40° to 50° C. until the benzoylacetic ester had dissolved. During this period, the mass solidified. The same product as in Example 1 was obtained in a highly pure form (pale yellow, melting point 105° C.).

Example 3

The procedure was as in Example 1. The resulting product was dissolved in 300 ml of diglyme, 25 g of magnesium oxide were added and the mixture was heated at 110° C. for 3 hours. Thereafter, 150 ml of 37% strength aqueous hydrochloric acid were added and the mixture was heated under reflux for 6 hours and discharged into 400 ml of water. The precipitate which had separated out was filtered off with suction, washed with water and isopropanol and dried. 122 g of N-(4-fluorophenyl)-6-fluoro-7-chloro-1,4-dihydro-4-oxo-quinolone-3-carboxylic acid of 99% purity were obtained. This corresponds to a yield of 73% of theory, based on the formimino ether employed.

Example 4

132.5 g of methyl 2,4-dichloro-5-fluorobenzoylacetate were dissolved in 83.5 g of 4-fluorophenylformimino ethyl ether, one drop of trifluoromethanesulphonic acid was added and the mixture was initially heated at 60° C. for 3 hours. During this operation, the product solidified. Thereafter, the mixture was heated at 75° C. for a further hour, whereupon liquefaction occurred, and then at 90° C. for a further hour, and the ethanol formed was distilled off. The resulting product was dissolved in 500 ml of butoxyethanol and subjected to cyclization with 80 g of magnesium oxide at 116° to 120° C. After working up in accordance with Example 3, 144 g of the same product as in Example 3 were obtained. The yield was 85% of theory, based on the formimino ether employed.

Example 5

9.5 g of N-(2,4-difluorophenyl)-formimino ethyl ether were dissolved in 13.5 g of methyl 2,4-dichloro-5-fluorobenzoylacetate and the solution was left to stand at 50° to 60° C. for 3 days. 23 g of a pale yellow solid were obtained which, according to HPLC analysis, was 98% pure. It contained 1% each of the starting materials and had a melting point of 91° C. This product was recrystallized from an ethanol/water mixture to give 14 g of pure methyl 3-[N-(2,4-difluorophenyl)amino]-2-(2,4-dichloro-5-fluorobenzoyl)-acrylate having a melting point of 91° C. This corresponds to a yield of 70% of theory, based on the formimino ether employed.

Example 6

60 ml of ethylene glycol monobutyl ether, 37 g of N-(2,4-difluorophenyl)-formimino ethyl ether and 50 g of ethyl 2,4-dichloro-5-fluoro-benzoylacetate were heated at 60° to 65° C. for 5 hours. Ethanol and a little solvent were stripped off under 20 mbar. The mixture was then diluted with 150 ml of ethylene glycol monobutyl ether, 12 g of magnesium oxide were added and the mixture was heated at 110° C. for 10 hours. For working up, the reaction mixture was poured into a mixture of 150 ml of water and 50 ml of 37% strength aqueous hydrochloric acid, heated at the boiling point for 5 hours and diluted with water and the precipitate was filtered off with suction and washed with water and 2-propanol to give 49.5 g of 99% pure N-(2,4-difluorophenyl)-6-fluoro-7-chloro-1,4-dihydro-4-oxo-quinoline-3-carboxylic acid. This corresponds to 70% of theory, based on the formimino ether employed.

Example 7

88 g of N-(2-fluorophenyl)-formimino ethyl ether were initially introduced into the reaction vessel and 132 g of methyl 2,4-dichloro-5-fluorobenzoylacetate were added. The mixture was then heated at 100° C. for 90 minutes and 23 g of ethanol and a little imino ether were distilled off under 200 mbar. 195 g of methyl 3-[N-(2-fluorophenylamino)]-2-(2,4-dichloro-5-fluoro-benzoyl)- acrylate were obtained as a pale yellow product. According to the gas chromatogram, it contained about 1% each of ethanol and the imino ether employed.

What is claimed is:

1. A process for the preparation of a N-arylaminoacrylic acid derivative of the formula (I)

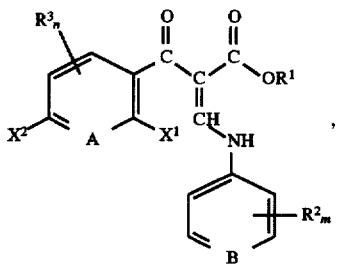

in which

R$^1$ denotes hydrogen or C$_1$–C$_6$-alkyl,

R$^2$ and R$^3$ independently of one another each denote fluorine, chlorine, bromine, trifluoromethyl, cyano, nitro, C$_1$–C$_6$-alkoxy, hydroxyl, imidazolyl, triazolyl or C$_7$–C$_{10}$-aralkoxy or R$^2$ and R$^3$ together denote an —O—, —CH$_2$—, —CH$_2$O—, —O—CH—O— or —O—CH$_2$—CH$_2$—O— radical, X$^1$ and X$^2$ independently of one another each denote fluorine, chlorine or bromine, A denotes CH, N or CR$^3$, where R$^3$=fluorine, chlorine, bromine, trifluoromethyl, cyano, nitro, C$_1$–C$_6$-alkoxy, hydroxyl, imidazolyl, triazolyl or C$_7$–C$_{10}$-aralkoxy, B denotes CH, N or CR$^2$, where R$^2$=fluorine, chlorine, bromine, trifluoromethyl, cyano, nitro, C$_1$–C$_6$-alkoxy, hydroxyl, imidazolyl, triazolyl or C$_7$–C$_{10}$-aralkoxy, m denotes zero, 1, 2 or 3 and n denotes zero, 1 or 2, in which a benzoylacetic acid derivative of the formula

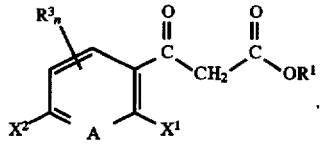

in which

R$^1$, R$^3$, X$^1$, X$^2$, A and n have the meaning given for formula (I), is reacted with an N-arylimino ether of the formula

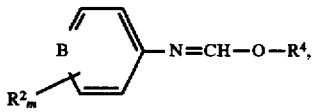

in which

R$^2$, B and m have the meaning given for formula (I) and

R$^4$ represents C$_1$–C$_6$-alkyl.

2. The process of claim 1, in which in the formulae (I) and (II),

R$^1$ represents C$_1$–C$_4$-alkyl,

R$^3$ represents fluorine or chlorine,

X$^1$ and X$^2$ independently of one another each represent fluorine or chlorine, A represents CH or CR$^3$, where R$^3$=fluorine or chlorine, B represents CH, N or CR$^2$, where R$^2$=F, Cl, Br or nitro, and n represents zero or 1, in the formulae (I) and (III), R$^2$ represents fluorine and m represents zero or 1, and, in formula (III), R$^4$ represents C$_1$–C$_4$-alkyl.

3. The process of claim 1, which is carried out at 30° to 130° C.

4. The process of claim 1, which is carried out without a solvent.

5. The process of claim 1, which is carried out in the presence of toluene, chlorobenzene, dichlorobenzene, oligoethylene glycol monoalkyl ethers, oligoethylene glycol dialkyl ethers, dimethylformamide or N-methylpyrrolidone as a solvent.

* * * * *